US010709459B2

(12) United States Patent
Eckermann

(10) Patent No.: US 10,709,459 B2
(45) Date of Patent: Jul. 14, 2020

(54) ANTI-DUROTOMY KERRISON RONGEUR

(71) Applicant: Jan Eckermann, Corona Del Mar, CA (US)

(72) Inventor: Jan Eckermann, Corona Del Mar, CA (US)

(*) Notice: Subject to any disclaimer, the term of this patent is extended or adjusted under 35 U.S.C. 154(b) by 13 days.

(21) Appl. No.: 15/924,105

(22) Filed: Mar. 16, 2018

(65) Prior Publication Data
US 2018/0263636 A1 Sep. 20, 2018

Related U.S. Application Data

(60) Provisional application No. 62/472,102, filed on Mar. 16, 2017.

(51) Int. Cl.
A61B 17/16 (2006.01)

(52) U.S. Cl.
CPC ...... *A61B 17/1604* (2013.01); *A61B 17/1611* (2013.01)

(58) Field of Classification Search
CPC . A61B 17/16; A61B 17/1604; A61B 17/1608; A61B 17/1611
See application file for complete search history.

(56) References Cited

U.S. PATENT DOCUMENTS

| 4,990,148 | A | * | 2/1991 | Worrick | A61B 17/1611 606/170 |
| 5,026,375 | A | * | 6/1991 | Linovitz | A61B 17/1611 30/349 |
| 5,273,519 | A | * | 12/1993 | Koros | A61B 17/1611 606/170 |
| 5,584,844 | A | * | 12/1996 | Weisshaupt | A61B 17/1611 606/170 |
| 6,520,979 | B1 | * | 2/2003 | Loubens | A61B 17/1611 606/205 |
| 8,556,899 | B2 | * | 10/2013 | Heinemann | A61B 17/1611 606/167 |
| 8,801,714 | B1 | * | 8/2014 | Bodor | A61B 17/1611 600/564 |
| 8,864,766 | B2 | * | 10/2014 | Weaver | A61B 17/1611 606/83 |
| 2004/0044346 | A1 | * | 3/2004 | Boury | A61B 17/1611 606/83 |
| 2006/0189995 | A1 | * | 8/2006 | Lancial | A61B 17/1611 606/83 |
| 2007/0265633 | A1 | * | 11/2007 | Moon | A61B 17/32078 606/83 |
| 2011/0213369 | A1 | * | 9/2011 | Weaver | A61B 17/1611 606/83 |

(Continued)

*Primary Examiner* — Eric S Gibson
(74) *Attorney, Agent, or Firm* — R. Scott Kimsey, Esq.

(57) ABSTRACT

A rongeur for cutting bone and other tissue includes a first shaft terminating in a footplate and a second shaft having a cutting edge. The first shaft and the second shaft are capable of reciprocal motion relative to one another, such that the cutting edge and footplate are moveable from a maximally-separated open position to a closed position. In the closed position, the cutting edge and the footplate may be in contact. The rongeur further includes a flange extending outwardly from either the footplate or the second shaft, or includes a first flange extending outwardly from the footplate and a second flange extending outwardly from the second shaft.

2 Claims, 6 Drawing Sheets

(56) References Cited

U.S. PATENT DOCUMENTS

| | | | |
|---|---|---|---|
| 2012/0010622 A1* | 1/2012 | Heinemann | A61B 17/1611 606/83 |
| 2012/0016401 A1* | 1/2012 | Faulhaber | A61B 17/1611 606/184 |
| 2012/0016402 A1* | 1/2012 | Weisshaupt | A61B 17/1611 606/184 |
| 2013/0041378 A1* | 2/2013 | Funnell | A61B 17/1611 606/83 |
| 2013/0041379 A1* | 2/2013 | Bodor | A61B 17/1611 606/83 |
| 2018/0263636 A1* | 9/2018 | Eckermann | A61B 17/1604 |

* cited by examiner

FIG. 1 -PRIOR ART-

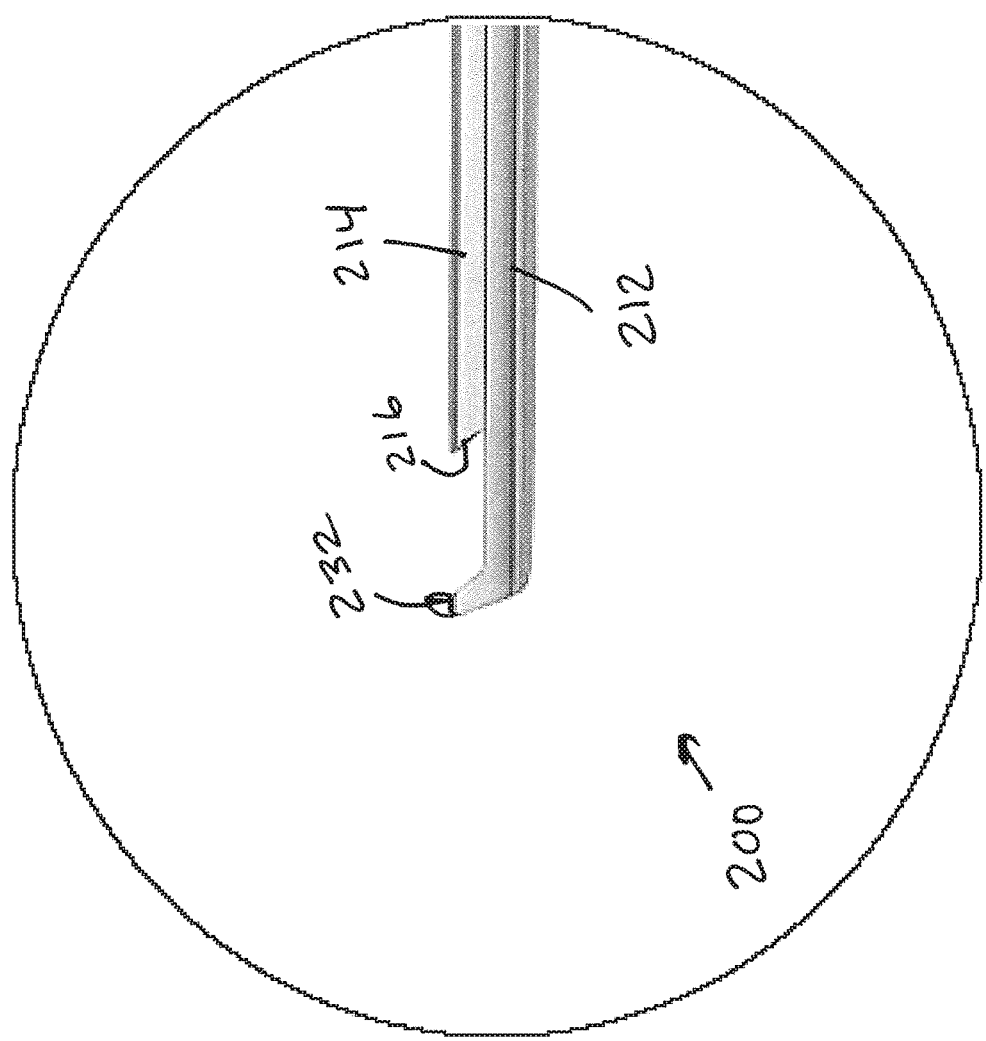

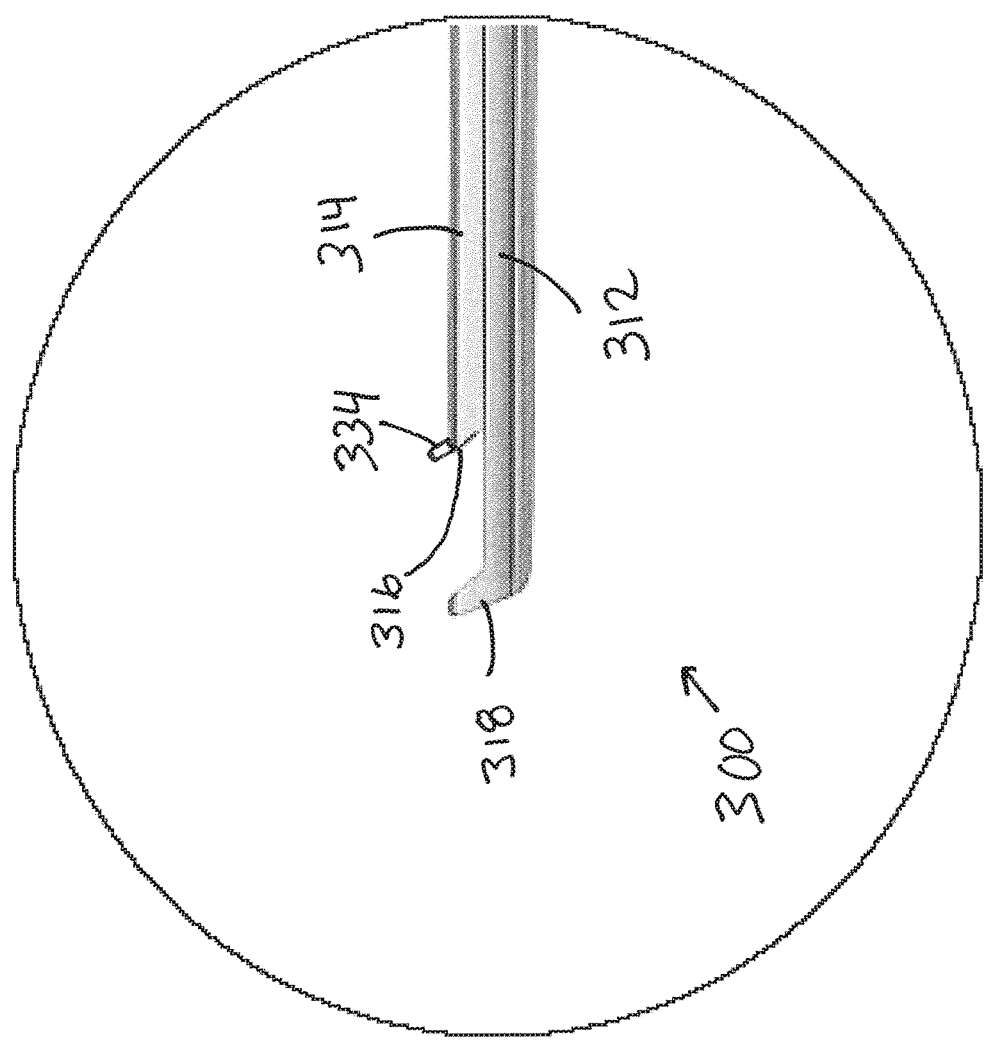

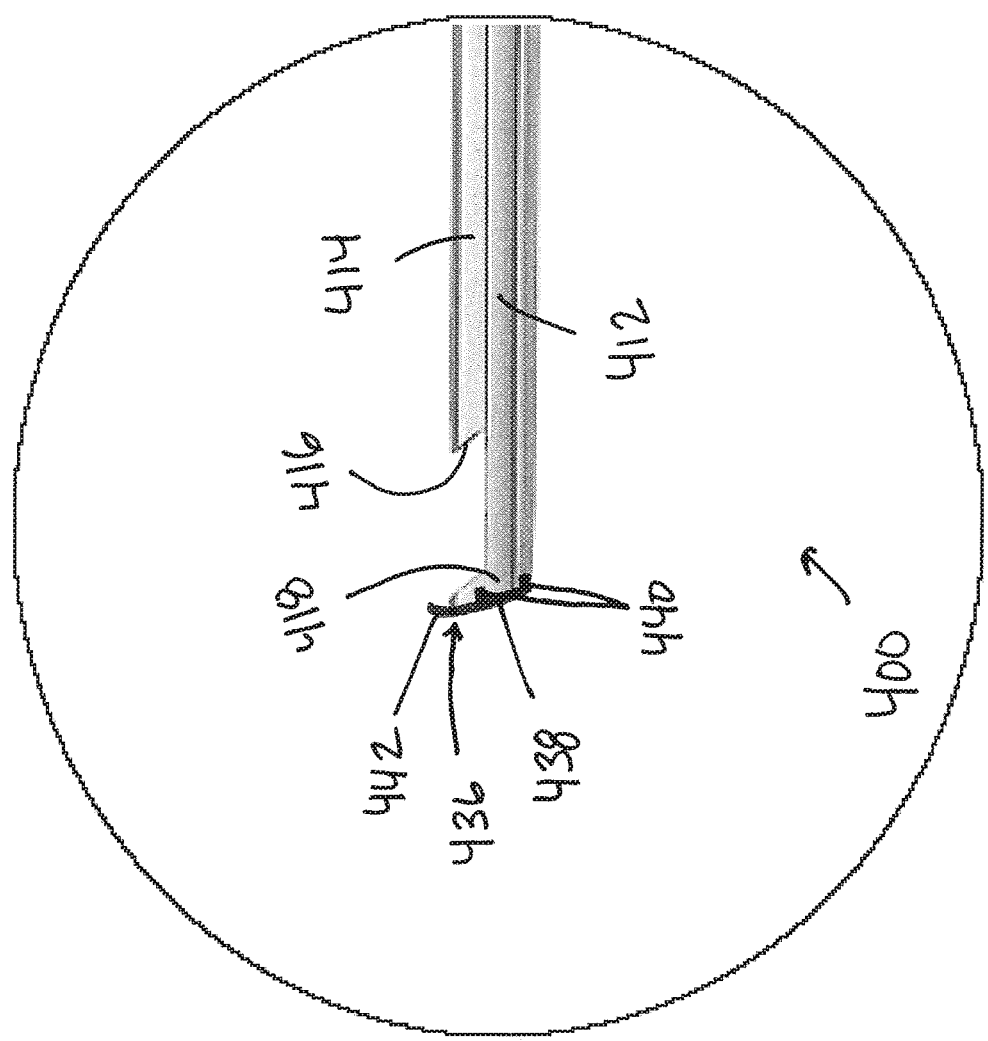

ANTI-DUROTOMY KERRISON RONGEUR

RELATED APPLICATIONS

The present application claims priority to U.S. Provisional Patent Application No. 62/472,102, filed Mar. 16, 2017 and entitled "Anti-Durotomy Kerrison Rongeur."

BACKGROUND AND FIELD

1. Field

The present disclosure relates generally to the field of surgical instruments, and more specifically to an improved Kerrison rongeur.

2. Background

Kerrison rongeurs are commonly used in spinal surgery, and to a lesser extent in cranial surgery, to take down bone overlying the dura mater of a patient being treated. In use, the leading edge of the bone to be taken down is positioned within the open portion of the distal end of the Kerrison rongeur. The surgeon then squeezes the handle of the Kerrison rongeur, moving the sliding portion of the device and causing it to be advanced through the bone to the stationary footplate of the instrument. The device severs or 'bites out' that portion of bone that was positioned within the open portion of the distal end of the device. The device is then removed from the surgical site so the excised bone fragment can be cleared from the instrument.

Incidental tear of the dural sac is a common problem during such procedures, and leads to a durotomy and accompanying cerebrospinal fluid (CSF) leak. Reported incidences of incidental durotomies range from 1% to 17% of such procedures, and at least one study of medical malpractice cases relating to spine surgery found that incidental durotomies accounted for the second most frequent complication in such surgeries.

SUMMARY OF THE DISCLOSURE

One aspect of the present disclosure provides a rongeur for cutting bone and other tissue. The rongeur includes a first shaft terminating in a footplate and a second shaft having a cutting edge. The first shaft and the second shaft are capable of reciprocal motion relative to one another, such that the cutting edge and footplate are moveable from a maximally-separated open position to a closed position. In the closed position, the cutting edge and the footplate may be in contact. The rongeur further includes a flange extending outwardly from either the footplate or the second shaft, or includes a first flange extending outwardly from the footplate and a second flange extending outwardly from the second shaft.

Another aspect of the disclosure provides that the flange extends from the footplate and is flush with an end thereof.

Another aspect of the disclosure provides that the flange has a curved leading edge.

Another aspect of the disclosure provides that the flange extends fully around the perimeter of the footplate.

Another aspect of the disclosure provides that the flange includes a curved outer profile such that it defines a hood.

Another aspect of the disclosure provides that the flange is integrally formed as part of a detachable protector. The detachable protector has at least one fastener configured to be removably attached to the footplate of the rongeur. The flange extends outward from the surface of the footplate, and adjacent thereto, when the protector is attached to the rongeur.

BRIEF DESCRIPTION OF THE DRAWINGS

FIG. 4 is a close side view of one alternative embodiment of a rongeur device of the present disclosure.

FIG. 5 is a close side view of another alternative embodiment of a rongeur device of the present disclosure.

FIG. 6 is a close view of a footplate and shaft of a rongeur device having a protector of the present disclosure associated therewith.

DETAILED DESCRIPTION

The terms "top," "bottom," "front," "rear," "forward," "rearward" or similar terms may be used in this disclosure. These terms are used to orient the reader to the illustrations provided, with the slide assembly representing the "top" of the device, the footplate representing the "front" of the device, and the thumb and forefinger support representing the "rear" of the device. These terms are not intended to be limiting, and do not necessarily correspond to the orientation of the present device in use for any given surgical procedure.

Figure 1:
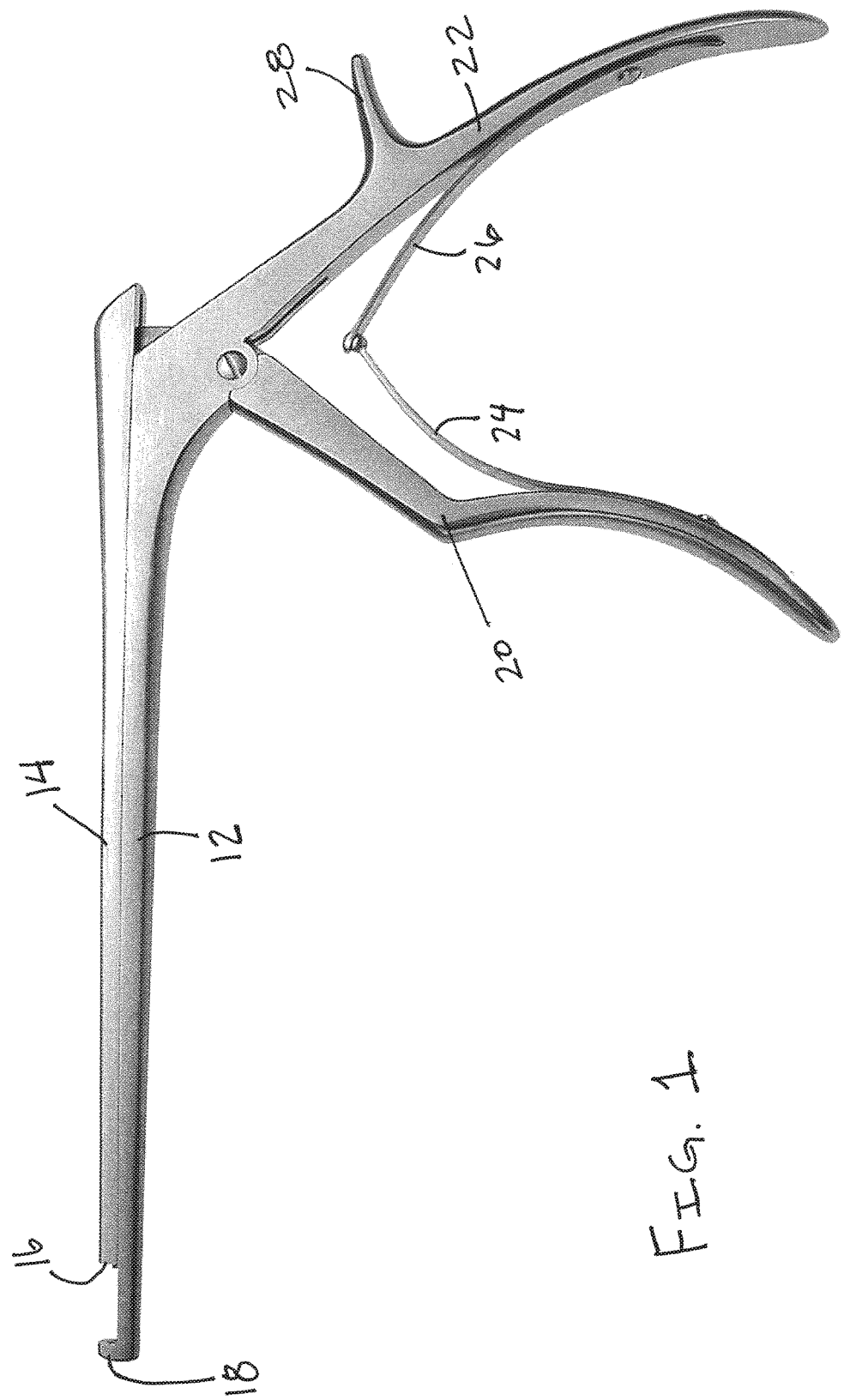
FIG. 1 is a side view of a prior art rongeur device.

FIG. 1 illustrates one version of a typical rongeur device 10 commonly known in the art. The device is hand-held, and is used by a surgeon during surgery. The device includes a shaft 12, slide assembly 14, forward handle 20, rear handle 22, and first and second biasing members 24 and 26 disposed between the handles. Slide assembly 14 has a cutting edge 16, and shaft 12 terminates in a footplate 18. The prior art rongeur shown in FIG. 1 also includes a support, which a surgeon may grip between the thumb and forefinger, for example, while using the device. When a user squeezes the handles, thereby causing forward handle 20 to move relative to rear handle 22, slide assembly 14 moves along the length of shaft 12, shortening the gap between cutting edge 16 of slide assembly 14 and footplate 18 at the end of shaft 12. This gap forms the cutting area of the device. The biasing members between the handles maintain the gap between the stationary and moveable shafts at a predetermined distance when the rongeur is at rest, and also provide resistance when the device is in use by a surgeon.

Figure 2:
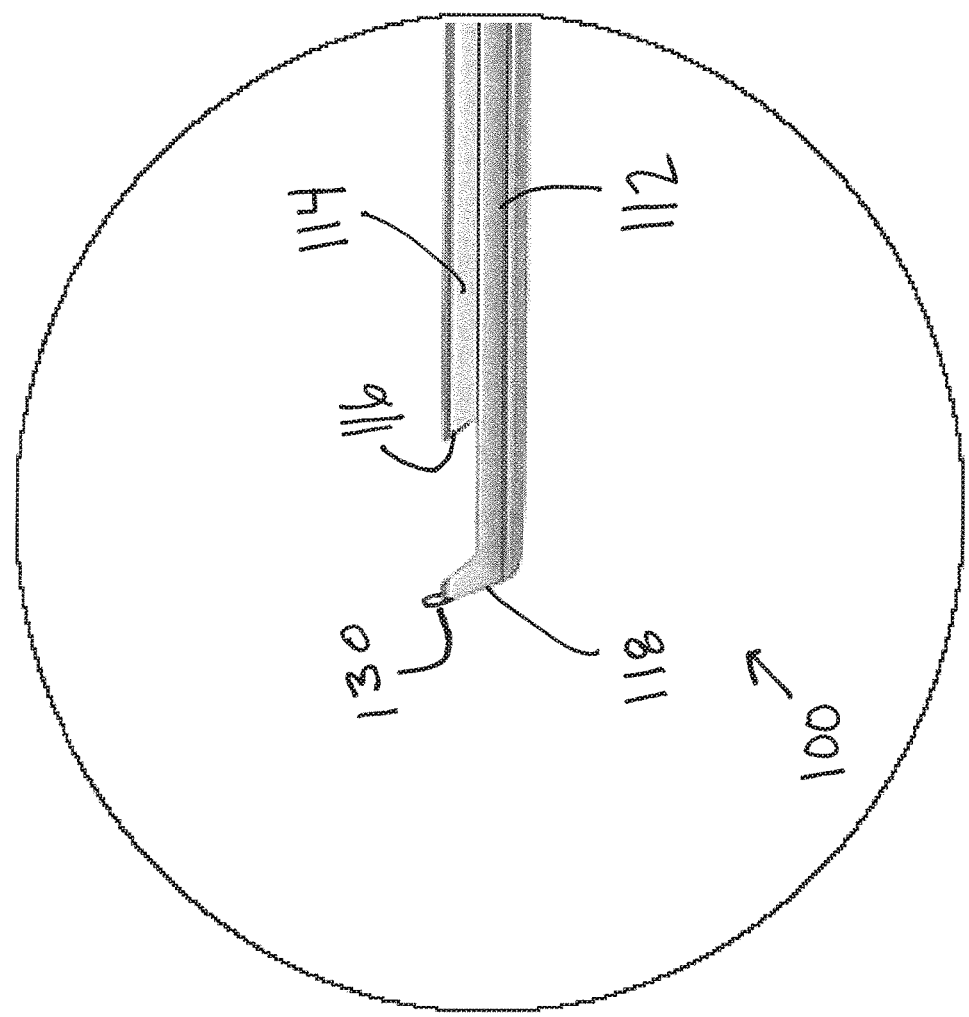
FIG. 2 is a close side view of one embodiment of a rongeur device of the present disclosure.

FIG. 2 is a close view of the forward end of one embodiment of a rongeur 100 of the present disclosure. Rongeur 100 incorporates the features of the prior art device, described above, and additionally includes a flange 130 extending from footplate 118. Flange 130 is operable to keep the dura mater at a distance from the cutting area when the cutting functionality of the device is used, thereby reducing the chance of an incidental durotomy when the gap between the cutting edge 116 and footplate 118 is closed.

Figure 3:
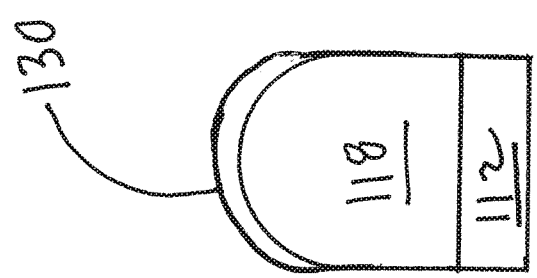
FIG. 3 is a cross-section view of a portion of one embodiment of a rongeur device of the present disclosure.

FIG. 3 provides a cross-section view of the device of FIG. 2, looking down the length of shaft 112 toward footplate 118. Flange 130 is shown extending beyond the boundaries of footplate 118. Flange 130 may be constructed from any suitable material, and may be formed integrally as part of footplate 118 or may be made from a separate material and attached thereto. The edges of flange 130 that may contact the dura mater or other tissue are preferably blunt or rounded. In some embodiments of the present device, flange 130 may be constructed from a softer material than rongeur 100 so as to further reduce the risk of damage to surrounding tissue. Although any suitable dimensions may be used in constructing a device of the present disclosure, it is preferred that flange 130 be as thin as possible without providing an edge that could easily damage tissue, and that the height of flange 130 be as small as possible while still allowing flange 130 to perform its function. A larger flanger 130 may be more restrictive than a smaller flange 130 in terms of the operative space in which the device may be used, simply because a device with a smaller profiles has greater clearance within the operative space. In some embodiments, for example, flange 130 may be about 1 mm in height. It is preferred that the leading edge (i.e. the edge facing toward the front of the device) of flange 130 be curved or sloped so not to damage tissue as the device moves forward into the operative site.

FIG. 4 is a close view of the forward end of one alternative embodiment of a rongeur 200 of the present disclosure, wherein instead of a flange extending from an end of footplate 218, a hood 232 is provided extending upwardly from footplate 218 and curving outward to cover the footplate. Hood 232 may be formed integrally with footplate 218 and may be a separate structure attached thereto. It is preferred that hood 232 have a rounded external profile and that the edges thereof be blunt or rounded to reduce the likelihood of damage to surrounding tissue. Hood 232 may be solid and may define no interior space thereinside, or may be shaped generally as shown and include an interior space between the walls of the hood.

FIG. 5 is a close view of the forward end of still another alternative embodiment a rongeur 300 of the present disclosure, wherein an extending flange 334 is provided at or near the cutting edge 316 of slide assembly 314 rather than extending from footplate 318. When slide assembly 314 moves forward along shaft 312, closing the gap between cutting edge 316 and footplate 318, flange 334 operates to push the dura mater out of the way of the cutting action. As with the embodiments described above, flange 334 may be formed integrally with footplate 318 or may be formed from separate material and attached thereto. The edges of flange 334 are preferably rounded or blunt. The leading edge of flange 334 may be curved or sloped to aid in safely pushing dura mater or other tissue aside when the device moves into the operative space.

FIG. 6 depicts a detachable protector 436 of the present disclosure for use with a rongeur device as shown. Detachable protector 436 includes a base 438, attachment arms 440, and a protruding top 442 that extends above the upper edge of footplate 418. It is contemplated that protector 436 be securely attached to footplate 418, preferably through structures in footplate 418 that correspond to attachment arms 440, allowing the attachment arms to maintain a secure grip on footplate 418 until the user of the device desires to remove protector 436 from the device. Protector 436 may be constructed from any suitable material, and the edges thereof are preferably rounded or blunt as with other embodiments of the present disclosure. The leading edge of the protector is preferably curved or sloped to safely push away dura mater or other tissue when the device moves into the operative space.

It is contemplated that the dimensions of the flange structures associated with the improved rongeur device described herein may be varied according to the needs or desires of the user. This includes the thickness of the flange, the distance at which it extends beyond the footplate or slide assembly of the device, the extent to which it protrudes to the side of the footplate, and so on. Variance in the dimensions can be used to adjust the distance between the cutting area of the device and the dura mater of the patient. Thus, the surgeon can take down bone closer or further from the dura mater, while still maintaining protection against an incidental durotomy. In the embodiment utilizing a detachable protector, it is contemplated that various sizes and shapes of protector may be available to the user for use with a single rongeur, such that the user can simply detach one protector and attach another according to need.

In still other embodiments of the present rongeur device, the footplate may include a slidable portion that is moveable in an upward and downward direction—upward to create an extended flange similar to that described above, and downward to remove the extendable flange and return the device to the prior art configuration.

In some embodiments of the present disclosure, the lip or flange extending from the footplate of the device may extend fully around the perimeter of the footplate. It is contemplated that the flange may extend to a consistent height from the footplate all the way along its length, or that the flange may differ in height along its length. Further, the flange may have a smooth, uniform outer edge, or may have a variable edge of any suitable geometric configuration.

Another alternative embodiment of the present disclosure may include suction capability built in to the disclosed rongeur. It is contemplated that a suction-capable device may include the extended lip or flange described above, or may be provided without it. An internal bore through which suction can be applied may extend through either of the handles of the device, and into the corresponding shaft or slide assembly, terminating with an opening at or near the tip of either the shaft or the slide assembly. The handle through which the bore is provided may be configured to attached to an external suction source, thereby drawing suction through the internal bore running through the rongeur. The device may be provided with a mechanism for the surgeon to easily enable or disable suction through the device, such as via a valve or other mechanism operable by the surgeon. When a cutting action is performed using the rongeur, suction at or near the site of the cut draws the cut material (and other tissue or fluids) away from the surgical site and through the internal bore of the device, as well as through the attached suction connector. This allows the surgeon to keep the surgical area free of blood, debris, or other tissues and fluids, and to therefore have a better view of the surgical site during the surgery.

It is contemplated that the embodiments of the present disclosure described and shown herein are exemplary and are not intended to limit the present disclosure. Various modifications to what is described and shown herein will be readily apparent to those of skill in the art upon reading this disclosure, and such modifications are considered to be within the scope of the present disclosure.

The invention claimed is:
1. A rongeur for cutting bone or other tissue comprising:
a body comprising a first shaft terminating in a footplate and a second shaft comprising a cutting edge, wherein the first shaft and the second shaft are capable of reciprocating motion relative to one another such that the cutting edge and the footplate are moveable from a maximally-separated open position to a closed position; and
a flange extending outwardly from one of said footplate and said second shaft, wherein the flange comprises a curved outer profile such as to define a hood.

2. A rongeur for cutting bone or other tissue comprising:
a body comprising a first shaft terminating in a footplate and a second shaft comprising a cutting edge, wherein the first shaft and the second shaft are capable of reciprocating motion relative to one another such that the cutting edge and the footplate are moveable from a maximally-separated open position to a closed position; and
a flange integrally formed as part of a detachable protector comprising at least one fastener configured to be removably attached to the footplate of the rongeur, wherein the flange extends from a surface of the footplate of the rongeur when the protector is attached thereto.

* * * * *